United States Patent [19]

Kerschner et al.

[11] Patent Number: 5,153,348
[45] Date of Patent: Oct. 6, 1992

[54] TRANSESTERIFICATION ROUTE TO QUATERNARY AMMONIUM SUBSTITUTED CARBONATE ESTERS

[75] Inventors: Judith L. Kerschner, Hawthorne; Sharon M. Jureller, Little Ferry, both of N.J.

[73] Assignee: Lever Brothers Company, Division of Conopco, Inc., New York, N.Y.

[21] Appl. No.: 582,271

[22] Filed: Sep. 14, 1990

[51] Int. Cl.$^5$ .............................................. C07C 69/96
[52] U.S. Cl. ................................... 558/276; 558/274; 558/28
[58] Field of Search ................ 546/348, 184; 544/106, 544/3, 358; 548/400, 335, 250, 519; 558/274, 276, 28

[56] References Cited

U.S. PATENT DOCUMENTS

| | | | |
|---|---|---|---|
| 2,691,017 | 10/1954 | Dornfeld | 252/99 |
| 4,217,438 | 8/1980 | Brunelle et al. | 558/265 |
| 4,349,486 | 9/1982 | Brunelle et al. | 558/274 |
| 4,739,076 | 4/1988 | Southwick | 548/519 |
| 4,751,015 | 6/1988 | Humphreys et al. | 260/247.3 |

Primary Examiner—David B. Springer
Attorney, Agent, or Firm—Milton L. Honig

[57] ABSTRACT

A process is reported for preparation of quaternary ammonium-type carbonate esters which are useful as bleach precursors in detergent compositions. The process involves transesterification of low molecular weight carbonates, e.g. diphenyl carbonate, with quaternary ammonium functionalized alcohols, e.g. choline chloride. Preferably the reaction is run in a high dielectric constant aprotic solvent such as acetonitrile. The reaction may also be conducted neat utilizing liquefied carbonate reactant as a solvent medium.

14 Claims, No Drawings

TRANSESTERIFICATION ROUTE TO QUATERNARY AMMONIUM SUBSTITUTED CARBONATE ESTERS

BACKGROUND OF THE INVENTION

1. Field of the Invention

The invention relates to a process for preparing quaternary ammonium substituted carbonate esters useful as bleach precursors in detergent compositions. 2. The Related Art Peroxygen compounds such as sodium perborate are ineffective at bleaching fabrics under wash-water temperatures below 60° C. Good low temperature performance can however be achieved through combination of the peroxygen compound with a precursor as activating agent.

A recently issued patent, U.S. Pat. No. 4,751,015 (Humphreys et al), reported an unusually effective family of bleach precursors identified as quaternary ammonium substituted peroxy carbonic acid esters. Various synthetic routes have been proposed to obtain these materials.

One route involves the reaction of an alcohol such as cholyl chloride with phosgene in an aprotic organic solvent to form a hydrogen chloride complex of a cholyl chloroformate. Subsequent thereto, the chloroformate is combined with a second hydroxylic material such as phenol sulfonate. See co-pending application Ser. No. 272,197 filed Nov. 16, 1988.

Another synthetic avenue is described in co-pending U.S. application Ser. No. 400,195, filed Aug. 29, 1989. Therein is reported the reaction of an aryl chloroformate with sulfur trioxide forming an aryl sulfonated chloroformate. This intermediate is then condensed with a quaternary ammonium substituted alcohol such as cholyl chloride.

There are several problems with the aforementioned synthetic schemes. Both require phosgene chemistry and the concomitant elimination of hydrogen chloride during the esterification steps. Hydrogen chloride is highly corrosive to equipment. Capital expense is therefore significantly increased. Pollution problems also arise with the generation of acid by-products. The phosgene route also forms considerable quantities of sodium chloride which are not easily removable from the desired products. Sodium chloride is hygroscopic and adversely impacts upon stability of the desired carbonate esters.

Transesterification has been proposed as a route to obtain carbonate esters. U.S. Pat. No. 2,691,017 (Dornfeld) reports syntheses of bis-aminoalkyl carbonate derivatives through transesterification of diethylcarbonate with alkylamino compounds followed by quaternization of the amine group. A disadvantage of this synthetic scheme is that at least two steps are required. Only after transesterification can the amine be functionalized into the quaternary ammonium salt.

Accordingly, it is an object of the present invention to provide an improved synthesis of quaternary ammonium type carbonate esters.

A more specific object of the present invention is to provide a route to quaternary ammonium type carbonate esters not involving generation of any hydrogen chloride by-products.

A still further object of the present invention is to provide a synthetic route to quaternary ammonium type carbonate esters through an environmentally friendly procedure wherein product cleanly and with minimal workup separates from the reaction medium.

These and other objects of the present invention will become more readily apparent upon consideration of the detailed description and examples which follow.

SUMMARY OF THE INVENTION

A process is provided for the preparation of quaternary ammonium carbonate esters of the formula:

wherein:

A is $Z^-$

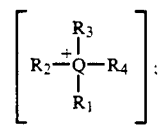

$R_1$, $R_2$ and $R_3$ are each a radical selected from the group consisting of alkyl, alkenyl, alkynyl, cycloalkyl, cycloalkenyl, alkaryl, aryl, phenyl, hydroxyalkyl, polyoxyalkylene, and $R_4OC(O)OL$;

or two or more of $R_1$, $R_2$ and $R_3$ together form an alkyl substituted or unsubstituted nitrogen-containing heterocyclic ring system;

or at least one of $R_1$, $R_2$ and $R_3$ is attached to $R_4$ to form an alkyl substituted or unsubstituted nitrogen-containing heterocyclic ring system;

$R_4$ is selected from a bridging group consisting of alkylene, cycloalkylene, alkylenephenylene, phenylene, arylene, and polyalkoxylene, and wherein the bridging group can be unsubstituted or substituted with $C_1$–$C_{20}$ atoms selected from alkyl, alkenyl, benzyl, phenyl and aryl radicals;

$Z^-$ is a monovalent or multivalent anion leading to charge neutrality when combined with $Q^+$ in the appropriate ratio and wherein $Z^-$ is sufficiently oxidatively stable not to interfere significantly with bleaching by a peroxy carbonic acid;

Q is nitrogen or phosphorous;

B is A, $R_1$ or L; and

L is selected from the group consisting of:

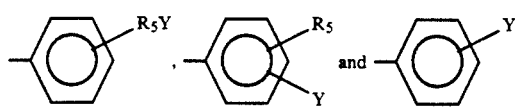

wherein $R_5$ and $R_6$ are a $C_1$–$C_{12}$ alkyl group, and Y is H or a water solubilizing unit selected from the group consisting of $-SO_3^-M^+$, $-COO^-M^+$, $-SO_2^-M^+$, $-N^+(R_5)_3X^-$, $-NO_2$, $-OH$, and $-N(O)(R_5)_2$ and mixtures thereof; $M^+$ is a cation which provides solubility to the ester, and $X^-$ is an anion which provides solubility to the ester; comprising the steps of:

(i) transesterifying a hydroxyl compound of the formula:

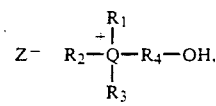 (II)

and optionally also L—OH, with $R_8OC(O)OR_8$ wherein $R_8$ is a substituted or unsubstituted phenyl, $C_1$–$C_{20}$ alkyl, and mixtures of radicals thereof; and (ii) separating the quaternary ammonium carbonate ester from other components of the reaction.

DETAILED DESCRIPTION

It has been found that quaternary ammonium functionalized alcohols readily undergo transesterification with low molecular weight carbonates to provide bleach precursors of Formula I. These products are described by the general formula:

$$A-O-\overset{\overset{O}{\|}}{C}-O-B \quad (I)$$

wherein:

A is $Z^-$

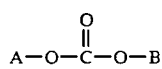

$R_1$, $R_2$ and $R_3$ are each a radical selected from the group consisting of alkyl, alkenyl, alkynyl, cycloalkyl, cycloalkenyl, alkaryl, aryl, phenyl, hydroxyalkyl, polyoxyalkylene, and $R_4OC(O)OL$;

or two or more of $R_1$, $R_2$ and $R_3$ together form an alkyl substituted or unsubstituted nitrogen-containing heterocyclic ring system; or at least one of $R_1$, $R_2$ and $R_3$ is attached to $R_4$ to form an alkyl substituted or unsubstituted nitrogen-containing heterocyclic ring system;

$R_4$ is selected from a bridging group consisting of alkylene, cycloalkylene, alkylenephenylene, phenylene, arylene, and polyalkoxylene, and wherein the bridging group can be unsubstituted or substituted with $C_1$–$C_{20}$ atoms selected from alkyl, alkenyl, benzyl, phenyl and aryl radicals;

$Z^-$ is a monovalent or multivalent anion leading to charge neutrality when combined with $Q^+$ in the appropriate ratio and wherein $Z^-$ is sufficiently oxidatively stable not to interfere significantly with bleaching by a peroxy carbonic acid;

Q is nitrogen or phosphorous;

B is A, $R_1$ or L; and

L is selected from the group consisting of:

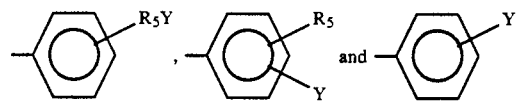

wherein $R_5$ and $R_6$ are a $C_1$–$C_{12}$ alkyl group, and Y is H or a water solubilizing unit selected from the group consisting of $-SO_3^-M^+$, $-COO^-M^+$, $-SO_2^-M^+$, $-N^+(R_5)_3X^-$, $-NO_2$, $-OH$, and $-N(O)(R_5)_2$ and mixtures thereof; $M^+$ is a cation which provides solubility to the ester, and $X^-$ is an anion which provides solubility to the ester.

Most preferred of the leaving groups L is the sulfonated phenol type. Especially useful is the 4-sulfophenol group. Sodium, potassium and ammonium cations are the preferred counterions to the sulfophenol structures.

In particular, it is desirable that $R_1$ be a short-chain $C_1$–$C_4$ alkyl radical, preferably methyl, while $R_2$ and $R_3$ may be a longer chain $C_7$–$C_{20}$ alkyl or alkylaryl, such as stearyl, lauryl, or benzyl group. With regard to the $R_4$ bridge between the quaternary nitrogen and carbonate groups, it is desirable that $R_4$ be a bridging group selected from $C_2$–$C_{20}$ alkylene, $C_6$–$C_{12}$ phenylene, $C_5$–$C_{20}$ cycloalkylene, and $C_8$–$C_{20}$ alkylenephenylene groups. Preferably, the alkylene groups should have 2 carbon atoms. Further, the bridging group can be unsubstituted or substituted with $C_1$–$C_{20}$ alkyl, alkenyl, benzyl, phenyl and aryl radicals.

Within the context of this invention, there may be compounds having the general structure (I) where $R_1$ and $R_4$ together or $R_1$ and $R_2$ together form an alkyl substituted or unsubstituted nitrogen-containing heterocyclic ring system. Representative of these systems are rings defining pyridine, morpholine, pyrrole, imidazole, triazole, tetrazole, pyrrolidine, piperidine and piperazine.

More specific compounds are listed in U.S. Pat. No. 4,751,015 which is herein incorporated by reference.

Generally the process comprises the steps of:

i) reacting a hydroxyl compound of the formula:

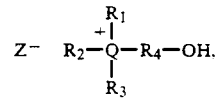 (II)

and optionally also L—OH, with a carbonate ester of the formula:

wherein $R_8$ is selected from a substituted or unsubstituted phenyl, $C_1$–$C_{20}$ alkyl and mixtures of radicals thereof; and (ii) separating the quaternary ammonium carbonate ester from other components of the reaction.

A variety of reactant $R_8OC(O)OR_8$ carbonate esters may be employed in the process of this invention. Advantageously, the $R_8$ radical is a phenyl, methyl or ethyl group with phenyl being preferred.. Substituents in the $R_8$ radical may include alkyl, aryl, sulfono, halo and mixtures of such groups.

An extremely efficient reaction is the one involving synthesis of bis[2-N,N,N-trimethylammonium)ethyl] carbonate dichloride. This product is obtained from transesterification of choline chloride, i.e. $[(CH_3)_3N^+CH_2CH_2OH]X^-$, with diphenylcarbonate.

Advantageously the process of this invention is conducted in an aprotic solvent media. Not only should the solvent be aprotic but it should possess a dielectric constant of at least about 5, preferably at least about 10, optimally at least about 35. Suitable solvents include acetonitrile, nitrobenzene, nitroethane, nitrotoluene, dimethylsulfoxide and dimethylformamide. Most preferred, however, is acetonitrile.

Solvent need not be present when the reaction is run. Normally solventless reactions are run at temperatures above the melting point of any reactants. For example, diphenyl carbonate when employed as reactant can serve as solvent at temperatures above 90° C., its melting point. Conversely, room temperature reactions usually require the presence of a separate solvent component. Moreover, high dielectric solvents are also required for quaternary ammonium functionalized alcohol reactants that are not readily soluble in the neat reaction medium. Choline chloride is such an example requiring acetonitrile for best results.

The synthesis can be conducted at atmospheric pressure and room temperature. Higher temperatures such as those generated by refluxing solvent may also be employed. Necessity of higher temperatures will depend upon the choice of reactants. For instance, choline chloride requires refluxing of acetonitrile because of its low solubility in organic media. The more soluble cholyl salts such as p-tolylsulfonate or dodecylbenzenesulfonate salts require only room temperature for reaction.

Transesterification according to this invention is facilitated by an acid or base catalyst to initiate and accelerate the reaction. Among suitable homogeneous catalysts are 4-(N,N-dimethylamino)pyridine and tetraisopropyl titanate. Other soluble amino and titanate compounds can also be effective. Homogeneous catalysts are advantageous since they remain behind in the solvent after product crystallizes from solution. Heterogeneous catalysts such as aluminum trichloride and di-t-butyl tin oxide were also found effective but these precipitated from solution along with product rendering separation difficult. Any number of Lewis acids or bases can be effective catalysts for the reaction including sodium phenoxide, other titanium, tin or aluminum halides, as well as other transition metal Lewis bases. Although the reaction works with dialkylcarbonate reactants, diphenyl carbonate is preferred because of better yields.

The following Examples will more fully illustrate the embodiments of this invention. All parts, percentages and proportions referred to herein and in the appended claims are by weight unless otherwise illustrated.

EXAMPLE 1

Preparation of Bis2-N,N,N-trimethylammonium)ethyl]Carbonate Dichloride

Into a 250 ml three necked round bottomed flask equipped with a condenser and a nitrogen inlet containing 50 ml degassed, dry acetonitrile was placed diphenylcarbonate (1.75g, 0.0082 mol), extremely dry choline chloride (2.34g, 0.0168 mol) and approximately 100 mg of 4-(N,N-dimethylamino)pyridine as a catalyst. The mixture was kept under a stream of nitrogen and refluxed overnight. After several minutes, a white precipitate appeared which increased over the course of the reaction. The flask was allowed to cool and the white solid product was filtered in a Buchner funnel and washed twice with diethyl ether. Product yield was 98-99%. The FTNMR in $D_2O$ was consistent with the product structure and showed the following peaks: Proton: $\delta$ 4.5-4.6 (m, O—$CH_2$—$CH_2$), 3.6-3.7 (m, $CH_2$—$CH_2$—N), 3.1 (s, N($\underline{CH_3}$)$_3$); Carbon-13: $\delta$ 149 ($\underline{C}$=O), 60 (O—$\underline{CH_2}$—N), 50 (N($\underline{CH_3}$)$_3$) The IR in Nujol showed a carbonyl stretch at 1750 cm$^{-1}$. The melting point was 230° C. (dec).

The reaction was also successfully conducted on a large (300 g) scale. Sufficient stirring and longer reaction times were employed for this scale-up.

EXAMPLE 2

Preparation of Bis[2(N,N,N-trimethylammonium)ethyl]Carbonate Bis-p-toluenesulfonate Into a 250 ml three-necked, round bottomed flask equipped with a condenser and a nitrogen inlet containing 75 ml degassed, dry acetonitrile was placed diphenylcarbonate (2.0 g; 0.0093 mol), dry choline p-toluenesulfonate (5.1 g; 0.0185 mol) and approximately 100 mg of 4-(N,N-dimethylamino)pyridine as a catalyst. The reaction was carried out at reflux temperature for 4-6 hours or at room temperature for 1-2 days. After reaction was complete, solvent was removed by rotary evaporation. The reaction mixture was then washed with acetone and diethyl ether to remove the phenol. The remaining white solid was analyzed to be bis[2-(N,N,N-trimethylammonium)ethyl] carbonate bis-p-toluenesulfonate (Yield—80-85%). The $^1$H FTNMR in $CD_3CN$ was consistent with the structure and showed the following peaks: $\delta$ 7.1 and 7.6 (d p-toluenesulfonate) 4.5-4.6 (m O—$CH_2$—$CH_2$). 3.6-3.7 (m, $CH_2$—$C\underline{H}_2$—N), 3.1 (s, N($\underline{CH_3}$)$_3$).

The reaction was also carried out successfully with the dodecylbenzenesulfonate and 4-hydroxybenzenesulfonate salts of choline. Both salts were prepared by the reaction of molar equivalents of choline bicarbonate and either dodecylbenzenesulfonic acid or 4-hydroxybenzenesulfonic acid in water followed by lyophilization of the salt.

EXAMPLE 3

The reaction of Example 1 was conducted in a variety of solvents having different dielectric constants. Based on the results outlined in the Table below, the reaction proceeded only where the solvent had a dielectric constant higher than 21.4 or where conducted without solvent.

| Solvent | % Yield | Dielectric Constant |
| --- | --- | --- |
| Acetonitrile | 95-98% | 38.8 |
| Acetone | No Rxn. | 21.4 |
| Acetone/Acetonitrile | 75-85% | >21.4 |
| Hexane | No Rxn. | 1.9 |
| Diphenylcarbonate (Melt - 100° C.) | 80-90% | ≈5 |

Catalyst = 4-(N,N-dimethylamino)pyridine
Choline Salt = Choline Chloride

The foregoing description and examples illustrate selected embodiments of the present invention. In light thereof, various modifications will be suggested to one skilled in the art, all of which are within the spirit and purview of this invention.

What is claimed is:

1. A process for the preparation of quaternary ammonium carbonate esters of the formula:

wherein:
A is Z—

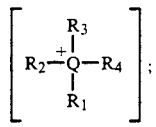

$R_1$, $R_2$ and $R_3$ are each a methyl radical;
$R_4$ is ethylene;
$Z^-$ is a monovalent or multivalent anion leading to charge neutrality when combined with $Q^+$ in the appropriate ration and wherein $Z^-$ is sufficiently oxidatively stable not to interfere significantly with bleaching by a peroxy carbonic acid;
Q is nitrogen;
B is A, $R_1$ or L; and
L is

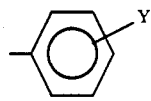

wherein Y is H or $-SO_3^-M^+$; $M^+$ is a cation which provides solublity to the ester;
the improvement comprising the steps of:
(i) transesterifying at a temperature of from 25° C. to about 230° C., a hydroxyl compound that is a choline salt of the formula:

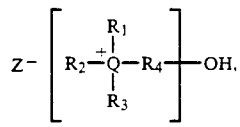

(II)

and optionally also L—OH with $R_8OC(O)OR_8$ wherein $R_8$ is phenyl in a solvent selected from the group consisting of liquefied reactant $R_8OC(O)OR_8$ and an aprotic substance having a dielectric constant of at least about 25; and
(ii) separating the quaternary ammonium carbonate ester from other components of the reaction.

2. A process according to claim 1 wherein the choline salt has a counterion selected from the group consisting of chloride, p-tolylsulfonate, dodecylbenzenesulfonate, 4-hydroxybenzenesulfonate sulfate and methosulfate.

3. A process according to claim 1 wherein the carbonate ester product is a salt of bis carbonate.

4. A process according to claim 1 wherein the carbonate ester product is 2-(N,N,N-trimethylammonium)ethyl 4-sulfophenyl carbonate.

5. A process according to claim 1 further comprising use of a reaction solvent which is aprotic and having dielectric constant of at least about 25.

6. A process according to claim 1 wherein the dielectric constant is at least about 30.

7. A process according to claim 1 wherein the solvent is selected from the group consisting of acetonitrile, nitrobenzene, nitroethane, nitrotoluene, dimethylsulfoxide and dimethyl formamide.

8. A process according to claim 1 conducted in the absence of any solvent other than liquefied reactant $R_8OC(O)OR_8$ carbonate.

9. A process according to claim 1 conducted at a temperature no higher than 40° C.

10. A process according to claim 1 wherein there is present an effective amount for transesterification of a catalyst selected from the group consisting of Lewis acids and Lewis bases.

11. A process according to claim 10 wherein the catalyst is a transition metal salt.

12. A process according to claim 11 wherein the transition metal salt has a cation selected from the group consisting of titanium, tin and aluminum.

13. A process according to claim 10 wherein the catalyst is an alkali metal alkoxide or phenoxide.

14. A process according to claim 10 wherein the catalyst is 4-(N,N-dimethylamino)pyridine.

* * * * *